United States Patent [19]

Livingston et al.

[11] Patent Number: 5,370,622
[45] Date of Patent: Dec. 6, 1994

[54] PROCTECTIVE CASE FOR A MEDICATION INFUSION PUMP

[75] Inventors: John H. Livingston, Los Angeles; Ward K. Frye, San Luis Obispo; Jeffrey F. Field, Northridge, all of Calif.

[73] Assignee: MiniMed Inc., Sylmar, Calif.

[21] Appl. No.: 233,924

[22] Filed: Apr. 28, 1994

[51] Int. Cl.⁵ .......................... A61M 1/00; A45F 5/00
[52] U.S. Cl. ..................... 604/151; 604/131; 224/247; 224/253
[58] Field of Search ............... 604/131, 151; 224/247, 224/253, 235, 240, 224; 607/149, 112

[56] References Cited

U.S. PATENT DOCUMENTS

| | | | |
|---|---|---|---|
| 4,215,689 | 8/1980 | Akiyama et al. | 604/151 |
| 4,411,267 | 10/1983 | Heyman | 607/149 |
| 4,801,011 | 1/1989 | Desdoigts | 224/253 |
| 5,065,918 | 11/1991 | Chan et al. | 224/247 |
| 5,097,122 | 3/1992 | Colman et al. | 604/151 |
| 5,170,817 | 12/1992 | Sander et al. | 137/343 |
| 5,244,463 | 9/1993 | Lorduer et al. | 604/151 |

Primary Examiner—John G. Weiss
Attorney, Agent, or Firm—Kelly Bauersfeld & Lowry

[57] ABSTRACT

A protective case is provided for receiving and supporting a medication infusion pump of the type used to deliver a selected medication such as insulin to a patient. The protective case comprises a transparent housing of impact resistant material for slide-fit reception of the pump, in combination with a seal cap for removable mounting onto the housing to define a substantially waterproof pump enclosure. The seal cap is formed from a resilient shock absorbing material and cooperates with additional shock absorber elements to resiliently support the pump within the housing. A catheter port is formed in the seal cap for sealed passage of a catheter tube extending from the pump to the patient. A belt clip is removably mounted onto the assembled case to prevent seal cap separation from the housing, and to provide a convenient structure for belt mounting of the protective case onto the body of patient.

17 Claims, 5 Drawing Sheets

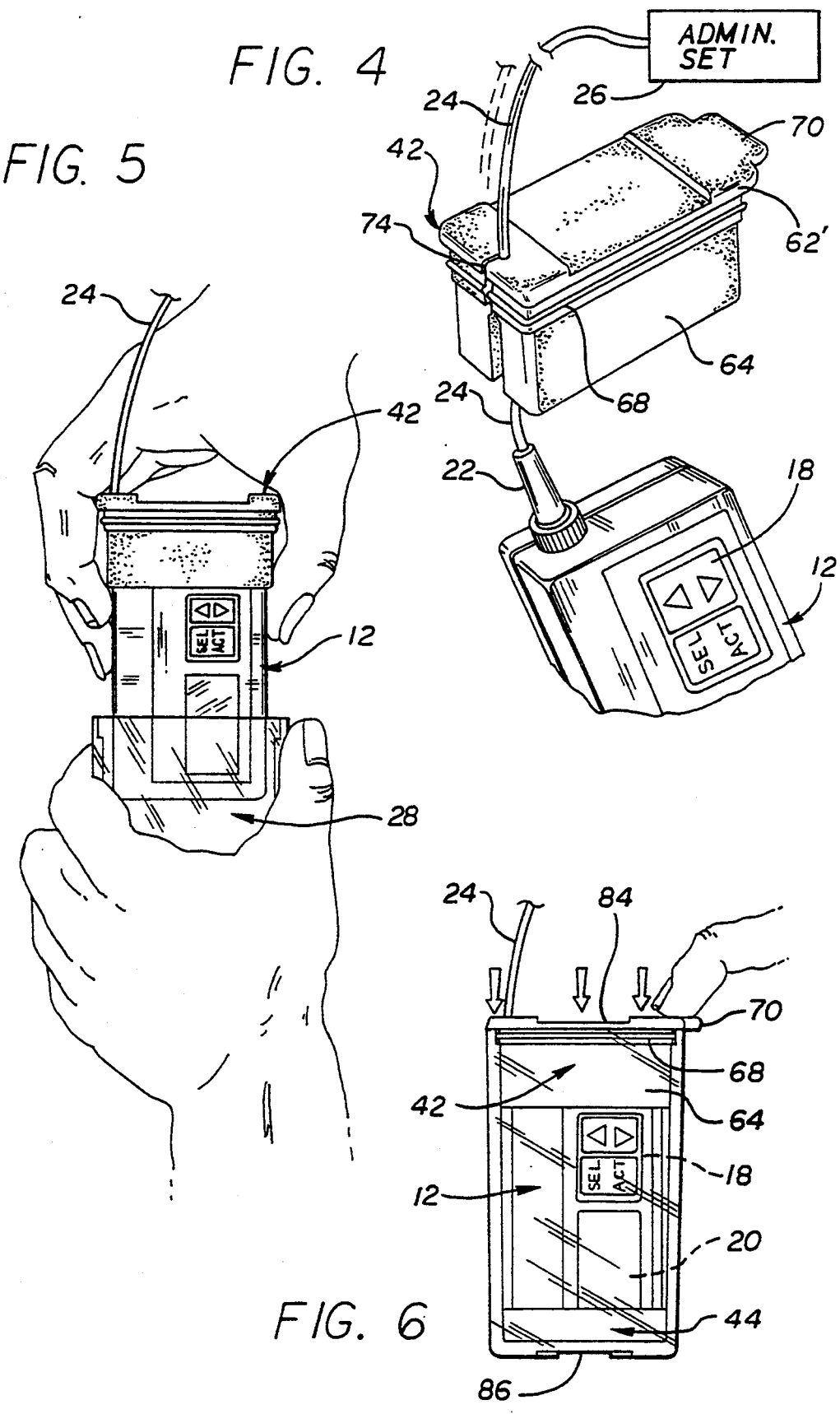

PROCTECTIVE CASE FOR A MEDICATION INFUSION PUMP

BACKGROUND OF THE INVENTION

This invention relates generally to a watertight and impact resistant protective case for receiving and supporting a compact medication infusion pump during normal pump operation to administer a selected medication to a patient. The protective case thus enables the patient to participate in a broad range of activities, including sports activities and/or aquatic activities wherein the pump is safeguarded against impact or water-caused damage.

Medication infusion pumps are generally known in the art, for use in delivering or dispensing a prescribed medication to a patient. In one common form, such devices comprise a relatively compact housing adapted to receive a syringe carrying a prescribed medication for administration to a patient through a catheter or the like. The infusion pump includes a small drive motor for controlled advancement of a syringe piston plunger to administer the medication to the patient. Programmable control means are normally provided for operating the drive motor continuously or at periodic intervals to obtain a closely controlled and accurate delivery of medication over an extended time period. Such infusion pumps are utilized to administer insulin and other medications, with exemplary pumps being marketed by MiniMed Technologies of Sylmar, Calif. under Model designations 504 and 506. See also U.S. Pat. Nos. 4,562,751; 4,678,408; and 4,685,903.

Medication infusion pumps of the general type described above provide significant advantages and benefits with respect to accurate delivery of the medication over an extended period of time. The infusion pump is often designed to be extremely compact and thus may be adapted to be carried by the patient. As a result, the medication can be administered with precision and in an automated manner, without significant restriction on the patient's mobility or life-style.

In the past, however, it has been necessary for the patient to exercise caution in order to prevent damage to the medication infusion pump as a result of impact shock or significant exposure to water. From a practical standpoint, these considerations have restricted the patient's activities to at least some degree. That is, to prevent impact damage, the patient is generally unable to participate in many sports activities wherein the pump might be exposed to significant impact with a ball, other athletes, etc. Similarly, patient participation in aquatic activities has been severely limited to prevent water damage to the internal components of the pump. This risk of water damage is particularly important, since undesired exposure of the pump to water occurs regularly in the course of a bath or shower. Theretofore, it has been necessary for the patient to be extremely careful to avoid impact or water-caused damage to the infusion, or otherwise disconnect the pump and catheter from the patient for the duration of any activity wherein pump damage might occur.

The present invention provides a relatively simple and easy to use, yet highly effective protective case for receiving and supporting a medication infusion pump, in a manner protecting the pump against impact or water-caused damage, without requiring disconnection of the infusion catheter from the patient. The present invention thus significantly expands the range of normal patient activities.

SUMMARY OF THE INVENTION

In accordance with the invention, a protective case is provided for receiving and supporting a medication infusion pump in a manner safeguarded against impact or water-caused damage and without requiring interruption of normal pump operation to administer a selected medication such as insulin to a patient. The protective case comprises a compact and lightweight enclosure of waterproof and impact resistant design wherein the protective case is adapted for convenient mounting onto the body of a patient.

In the preferred form of the invention, the protective case comprises a transparent housing formed from an impact resistant plastic material or the like, and having one open end with a size and shape for slide-fit reception of medication infusion pump. The pump is supported within the housing by shock absorber elements which space the walls of the pump from direct contact with the walls of the impact resistant housing. One of these shock absorber elements comprises a resilient seal cap for press-on mounting onto the open end of the housing, wherein the assembled seal cap and housing define a substantially waterproof enclosure. A catheter port is formed in the seal cap and accommodates sealed passage of a catheter tube extending from the infusion pump to the patient. Additional shock absorber elements include, in the preferred form, one or more resilient bumpers extending between the closed end of the housing and an adjacent end wall of the infusion pump.

A generally U-shaped belt clip is provided for snap-fit mounting onto the protective case. The belt clip defines a pair of legs adapted for snap-fit mounting over the opposite ends of the housing, wherein the belt clip retains the seal cap in position at the open end of the housing. Interfitting keys and keyway slots formed on the components accommodate a relatively tight and secure belt clip interconnection with the protective case.

The belt clip is adapted in turn for assembly with a belt or strap used for convenient mounting of the protective case onto the body of a patient. The belt is desirably adjustable in length and includes a snap buckle to permit rapid and convenient mounting, for example, around the patient's waist.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 4 is a fragmented perspective view illustrating assembly of a seal cap with a medication infusion pump;

FIG. 5 is a fragmented elevational view showing slide-fit reception of the medication infusion pump into the impact resistant housing;

FIG. 6 is a fragmented elevational view showing assembly of the seal cap with the housing;

DETAILED DESCRIPTION OF THE PREFERRED EMBODIMENT

Figure 1:
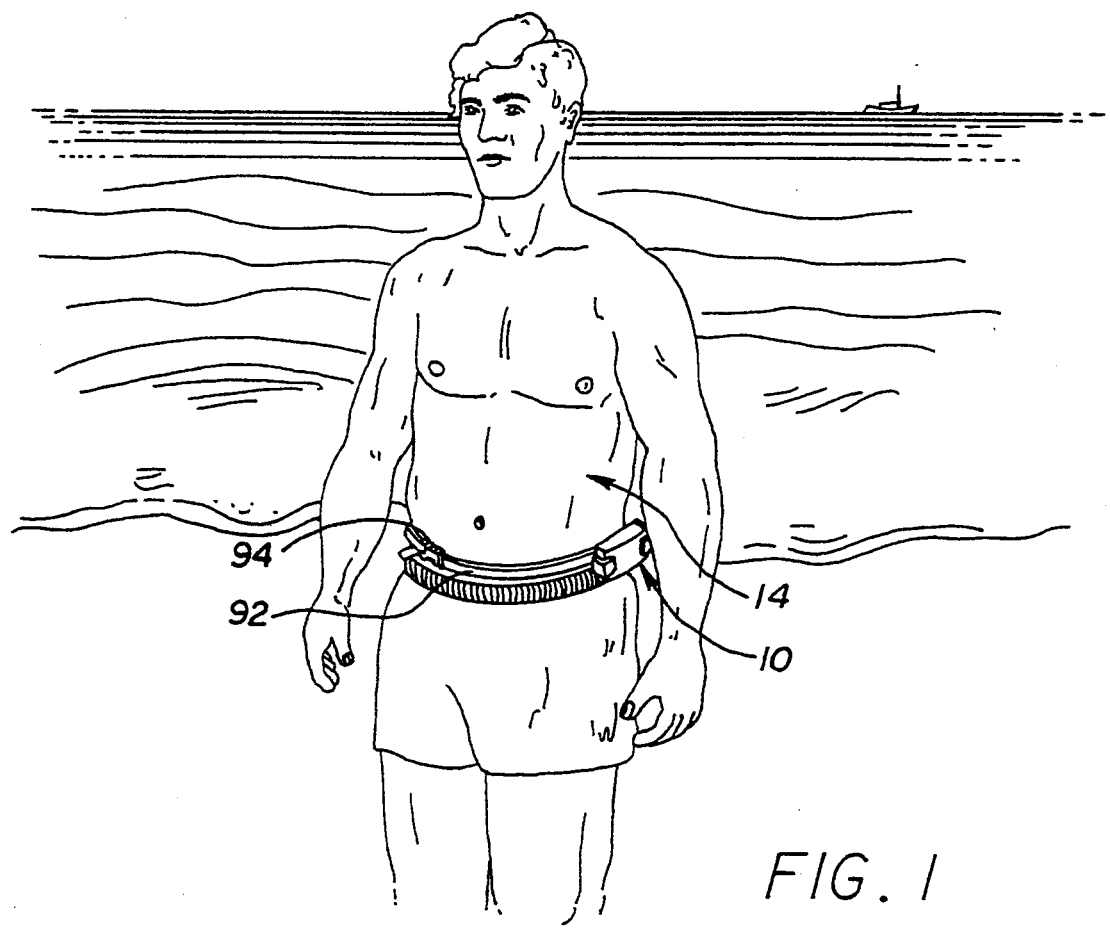
FIG. 1 is a perspective view illustrating the protective case embodying the novel features of the invention, for use in supporting a medication infusion pump in a protected manner on a patient.

As shown in the exemplary drawings, a protective case referred to generally by the reference numeral 10 is provided for supporting a medication infusion pump 12 (FIGS. 4–10) on the body of a patient 14 (FIG. 1). The protective case 10 is particularly designed to safeguard the pump 12 against damage from impact or exposure to water, without requiring disconnection of the pump from the patient or interruption in programmed delivery of medication to the patient. The protective case 10 thus enables the patient 14 to participate in a wide range of sports and/or aquatic activities.

The medication infusion pump 12 (FIGS. 4–10) has an overall construction and operation which is generally known in the art. More specifically, as shown in FIGS. 4–10, the infusion pump 12 is provided in the form of a relatively compact unit adapted to receive and support a syringe 16 (FIG. 10) or the like charged with a selected medication, such as insulin, to be administered to the patient 14. The pump 12 includes a front control panel 18 which can be appropriately manipulated in association with a display panel 20 to program a small infusion pump motor (not shown) for administering the medication to the patient. As shown in FIG. 4, the medication is delivered via a luer fitting 22, and a catheter tube 24 to an appropriate administration set 26, such as an administration set of the type shown and described in U.S. Pat. No. 4,755,173, which is incorporated by reference herein. Medication infusion pumps of this general type are described in U.S. Pat. Nos. 4,562,751; 4,678,408; and 4,685,903, which are also incorporated by reference herein. Such infusion pumps are available from MiniMed Technologies of Sylmar, Calif. under Model series designations 504 and 506.

The protective case 10 of the present invention expands the range of activities in which the patient can participate, without interrupting an important medication regimen and further without exposing the infusion pump to a significant risk of damage. For example, the protective case 10 enables the patient to participate in a wide range of normal aquatic activities, without concern for water-caused damage to the infusion pump. Moreover, the case 10 allows the patient to bathe or shower in a normal manner, without exercising extreme caution to prevent excessive water contact with the pump. Still further, the protective case supports the infusion pump 12 in a manner which protects the pump against impact-caused damage, so that the patient may also participate in a wide range of sports and other recreational activities without significant concern for preventing impact blows to the pump. Importantly, the infusion pump 12 can be placed into or removed from the protective case without requiring disconnection of the catheter tube 24 from the patient.

Figure 3:
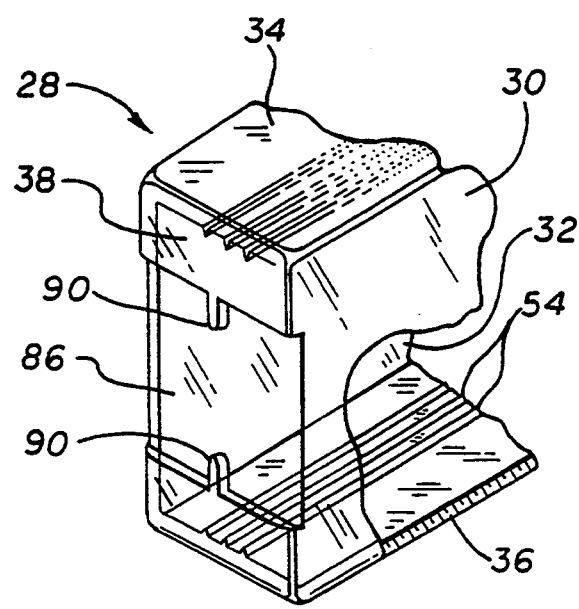
FIG. 3 is a fragmented perspective view depicting a closed end of an impact resistant housing for use in the invention.
Figure 2:
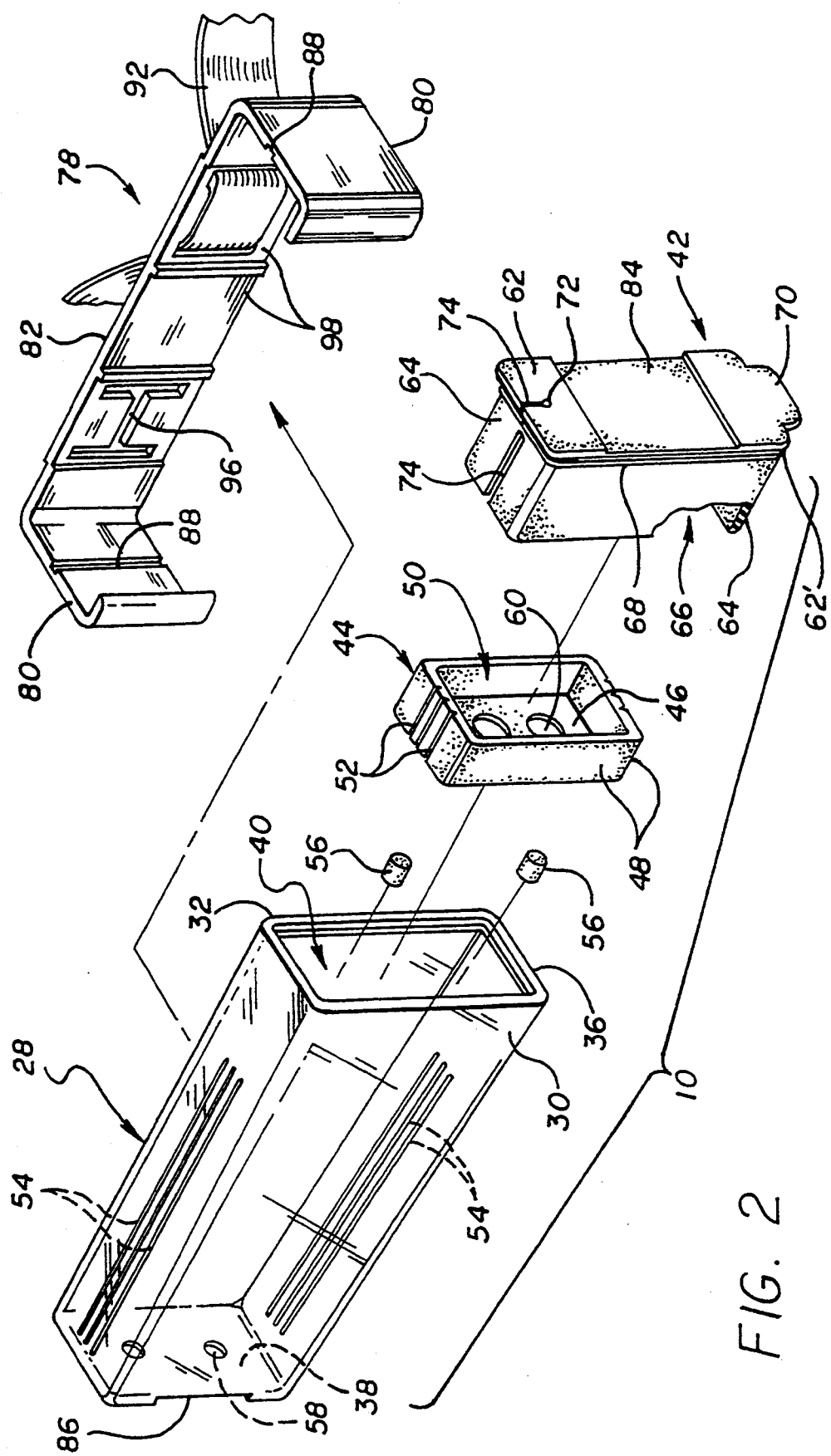
FIG. 2 is an enlarged exploded perspective view illustrating the protective case constructed in accordance with the invention.

As shown best in FIGS. 2 and 3, the protective case 10 comprises an open-ended housing 28 formed from a rigid impact resistant and scratch resistant material such as a molded and relatively hard polycarbonate plastic. The preferred housing material is transparent so that the infusion pump encased therein, as will be described, can be visually observed and monitored by the patient in a normal manner. The housing 28 includes front and rear walls 30 and 32 interconnected by top and bottom walls 34 and 36, wherein these walls are sized and shaped to provide a generally rectangular cross section which is slightly larger than the cross sectional geometry of the infusion pump 12. One end of the housing 28 is closed by an end wall 38, whereas the opposite end referred to by arrow 40 is open to permit slide-fit insertion of the infusion pump 12 into the housing interior.

Shock absorber elements are provided for resiliently supporting the infusion pump 12 within the housing 28, so that the walls of the pump 12 are physically and resiliently spaced on all sides from the housing 28. One of these shock absorber elements comprises a seal cap 42 which cooperates with the housing 28 to define a substantially waterproof enclosure within which the pump 12 is contained.

More particularly, a generally cup-shaped boot 44 formed from a resilient elastomer has a size and shape for close-fitting seated installation into the interior of the housing 28, in abutment with the closed end wall 38. This boot 44 includes a base wall 46 molded integrally with a perimeter wall 48 and cooperating therewith to define a shallow cavity 50 of generally rectangular cross sectional shape. The boot 44 is pressed into the housing 28 with the base wall 46 seated against the inboard side of the housing wall 38, and with the perimeter wall 48 seated against the housing walls 30, 32, 34 and 36 at a location adjacent to the end wall 38. Preformed grooves 52 may be provided in the perimeter wall 48 for registry with elongated ribs 54 molded on the inboard sides of the top and bottom housing walls 34, 36.

A pair of cylindrical or disk-shaped bumpers 56 are also provided within the housing 28 at the closed end wall 38. As shown in FIG. 2, these bumpers 54 are connected to the inboard side of the end wall 38, as by a suitable adhesive for mounting the bumpers within shallow preformed recesses 58. When installed, these bumpers 56 protrude through apertures 60 in the boot base wall 46, and project further a short distance into the boot cavity 50. These shock absorbing bumpers 56 are constructed from a high impact absorbing material, such as that marketed by Sorbothane, Inc., of Kent, Ohio, under the name Sorbothane.

The seal cap 42 is also formed from a resilient elastomer, and has a generally cup-shaped configuration for mating seated reception into the opposite open end 40 of the infusion pump 12. More specifically, the seal cap 42 also defines a base wall 62 formed integrally with a perimeter wall 64 and cooperating therewith to define a generally rectangular cross section cavity 66. The perimeter wall 64 is sized for press-fit reception into the open end 40 of the housing 28. The base wall 62 is shaped to project outwardly beyond the perimeter wall 64 to define a short lip 62' which overlies the marginal edges of the housing walls at the open end of the housing 28. One or more seal ribs 68 are desirably formed at the juncture of this lip 62' and the perimeter wall 64 to provide a positive watertight seal when the cap 42 is mounted onto the housing 28. A pull tab 70 is also provided at one edge of the cap 42 for easy manual grasping to facilitate pull-off removal of the cap from the housing 28, when desired.

A catheter port 72 is formed in the seal cap 42 for sealed passage of the catheter tube 24. This catheter port 72 is molded into the cap base wall 62 near one end thereof, and is formed with a diametric size which is slightly less than the outer diameter size of the catheter tube 24. A slit 74 is formed in the seal cap 42, to extend through the base wall 62 and the perimeter wall 64 into communication with the catheter port 72. Importantly, the catheter port 72 opens into the seal cap cavity 66 at a location within the boundary defined by the perimeter wall 64.

Installation of the infusion pump 12 into the protective case 10, defined by the assembled impact resistant housing 28 and seal cap 42, is shown in FIGS. 4–7. As shown, the catheter tube 24 is drawn manually through the side slit 74 into the catheter port 72 in the seal cap 42. Thereafter, the seal cap 42 is seated upon the adjacent end of the infusion pump 12. In this regard, the perimeter wall 64 of the seal cap 42 includes an internal shoulder 76 (FIG. 7) to define a leading edge portion of the cavity 66 of expanded cross sectional size for receiving and engaging the luer end of the pump 12. With this construction, the luer fitting 22 is positioned within the cap cavity 66, and a length of the catheter tubing 24 is also looped within the cavity 66 before passage through the catheter port 72 to the exterior of the case. The length of the catheter tubing 24 looped within the seal cap 42, as viewed FIG. 7, conveniently defines a stress relief segment.

The seal cap 42 is then installed, in assembled relation with the pump 12, onto the open end of the impact resistant housing 28 (FIG. 5). In this regard, the infusion pump 12 is slide-fitted into the housing 28 for seated reception of the opposite end of the pump into the boot cavity 50 with the leading end of the pump 12 pressed against the bumpers 56. The seal ribs 68 on the seal cap 42 are pressed into the open end of the housing 28, and these seal ribs may be coated with a water resistant seal agent, such as petroleum jelly, to enhance the watertight seal between the housing 28 and seal cap 42. Importantly, press-fit installation of the seal cap 42 into the open end of the housing 28 effectively pinches the cap material against the catheter tube 24 to provide a watertight seal without obstructing medication passage through the catheter tube. This pinching action effectively prevents leakage past the exterior of the catheter tube or through the slit 74.

Figure 7:
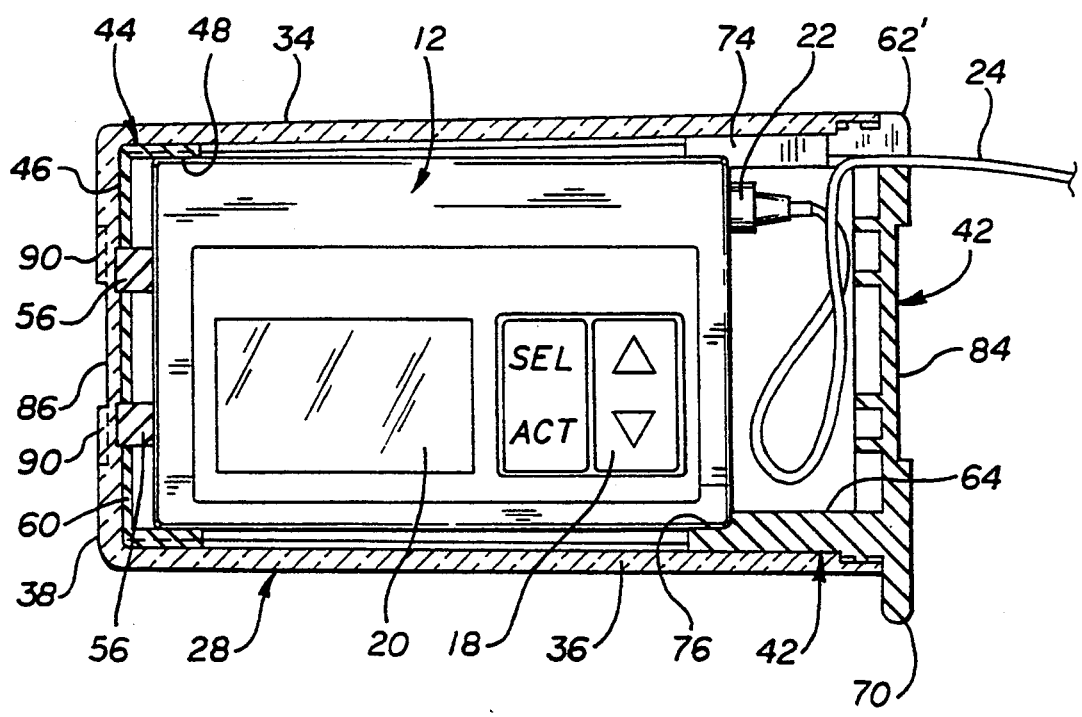
FIG. 7 is an enlarged vertical sectional view illustrating the medication infusion pump protectively supported within the assembled protective case.

As shown in FIG. 7, the encased infusion pump 12 is physically supported by the resilient shock absorber elements including the boot 44, bumpers 56 and seal cap 42. In other words, the pump 12 is spaced on all sides from the impact resistant material of the housing 28. The bumpers 56 space the pump from the closed end wall 38, and the perimeter walls 48 and 64 of the bolt 44 and cap 42 support the opposite ends of the pump in spaced relation with the housing walls 30, 32, 34 and 36. Thus, impacts to the housing 28 are effectively isolated from the pump 12. Although the material used for the boot 44 and cap 42 may vary, one preferred material is marketed by Concept Polymers, Inc. of Sarasota, Fla. under the name C-Flex.

Figure 8:
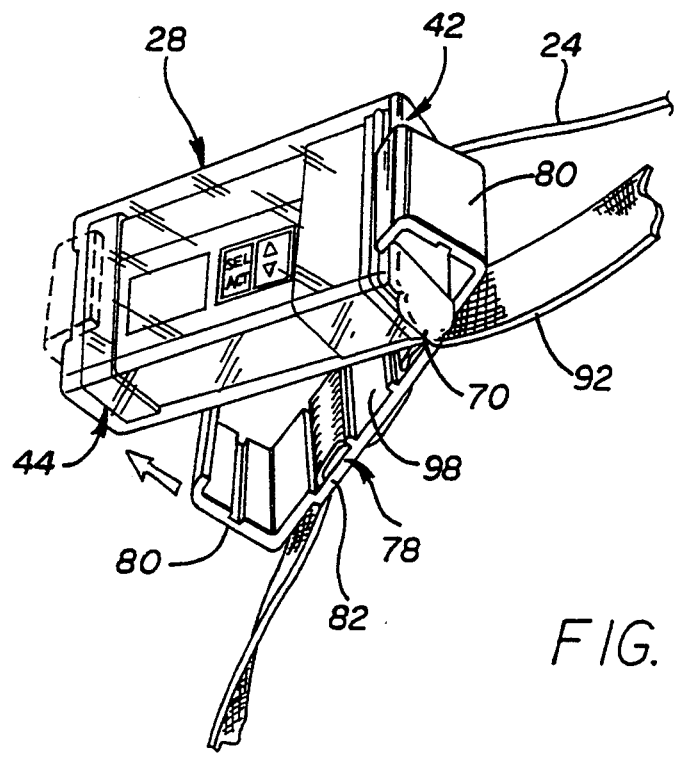
FIG. 8 is a fragmented perspective view showing snap-fit mounting of a belt clip onto the assembled case.
Figure 10:
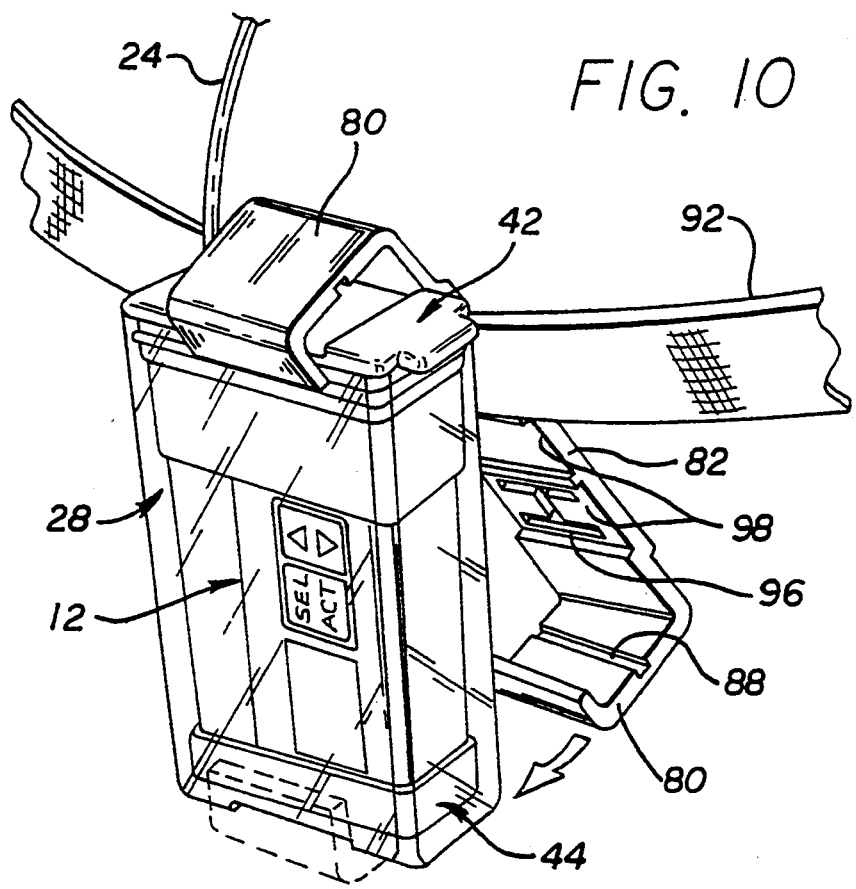
FIG. 10 is a fragmented rear perspective view showing the assembled protective case and belt clip.
Figure 9:
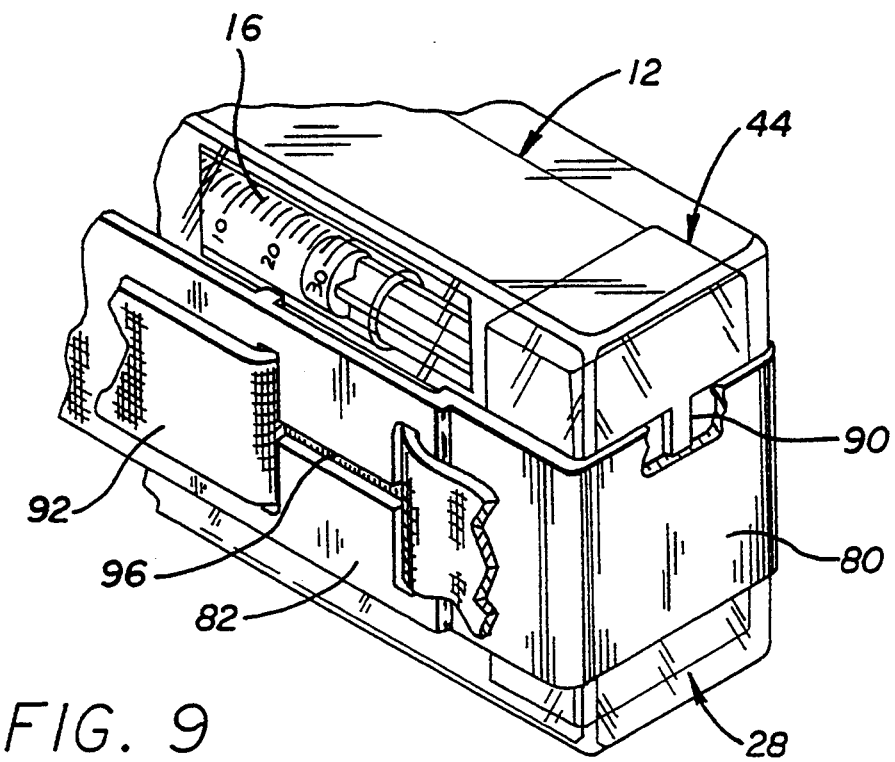
FIG. 9 is a fragmented perspective view illustrating belt clip mounting of the protective case onto the body of a patient in an alternative orientation.

A belt clip 78 is provided for positively retaining the seal cap 42 on the housing 28, while additionally providing a convenient structure for belt mounting of the entire device onto the body of a patient 14. The belt clip 58 shown in the exemplary drawings has a generally U-shaped construction defining a symmetric pair of opposed legs 80 interconnected by a central segment 82 (FIGS. 2 and 8). The belt clip 78 is constructed from a relatively sturdy molded plastic having sufficient flexibility for relatively easy snap-fit mounting with the legs 80 extending over the opposite ends of the housing 28. That is, one of the legs 80 is fitted over the seal cap 42, whereas the opposite leg 80 is fitted over the closed end wall 30 of the housing 28. Both belt clip legs include an inturned forward edge for clamp-on engagement with the protective case.

The legs 80 of the belt clip 78 seat within shallow channels 84 and 86 formed in the exterior surfaces of the seal cap 42 and the housing end wall 38. The channel 84 in the seal cap is offset to one side of the catheter port 72 to prevent the belt clip from occluding the catheter tube 24. In addition, each leg 80 is also conveniently provided with an internal recessed slot or keyway 88 for matingly receiving one or more keys 90 (FIG. 3) formed on the housing end wall 38. In this regard, while the belt clip legs 80 are desirably formed in a symmetric configuration, normal plastic molding procedures require the housing 24 to be formed with a minor draft angle, such that the cross sectional size of the housing increases slightly toward the open end 40. The key-lock connection between the keys 90 and the keyway 88 provides a secure and stable interlocked connection without rattle or a perception of a loose fit, despite dimensional variations attributable to molding draft angle.

The central segment 82 of the belt clip 78 is adapted for convenient attachment to a mounting belt 92 to be worn on the body of the patient 14. In the preferred construction, the belt 92 includes a convenient releasible buckle 94 (FIG. 1) and may be length-adjusted to fit an individual patient. The belt 92 is adapted to be threaded through one or more belt loop passages 96 (FIG. 2) formed in the central segment 82 of the belt clip. In this regard, the belt 92 can be attached to the belt clip 78 for mounting the case 10 in a generally horizontal orientation on the patient (FIGS. 1 and 8). In the alternative, the belt clip central segment 82 may be shaped to define a plurality of internal channels 98 through which the belt 92 can be fitted for vertical orientation mounting of the pump as viewed in FIG. 9.

In accordance with further aspects of the invention, the transparent material forming the case housing 28 permits normal visual observation and monitoring of the infusion pump 12. That is, the front display panel 20 on the pump 12 may be observed through the material of the protective case so that informational displays may be observed and monitored in a normal manner. In addition, the vertical height of the belt clip 78 is designed to be substantially less than the height of the encased pump 12, so that observation of a medication-containing syringe 84 remains unobstructed.

The protective case 10 of present invention thus provides a relatively simple and easily manipulated device for receiving and supporting a medication infusion pump on the body of a patient for normal uninterrupted operation, safeguarded against impact-caused damage and/or damage attributable to exposure to water during aquatic activities, etc. The pump 12 can be placed into the protective case 10 quickly and easily without interrupting administration of medication. The protective case 10 is also buoyant. In addition, the pump 12 can be removed from the protective case 10 in an equally simple manner, without interrupting medication delivery.

A variety of further modifications and improvements to the protective case of the present invention will be apparent to those skilled in the art. Accordingly, no limitation on the invention is intended by way of the foregoing description and accompanying drawings, except as set forth in the appended claims.

What is claimed is:

1. A protective case for a medication infusion pump having a catheter tube extending therefrom for delivery of a selected medication from he pump to a patient, said protective case comprising:
   a housing formed from an impact resistant material, said housing having one closed end and an opposite open end;
   shock absorber means for resiliently supporting the pump within said housing;
   a seal cap removably mounted on said housing over said open end thereof, said seal cap having a catheter port formed therein for sealed passage of the catheter tube from the pump to the exterior of said housing; and
   means for retaining said seal cap on said housing, said retaining means comprising a belt clip, and further including a belt for removable connection to said belt clip, said belt being adapted to support said belt clip together with said housing and said seal cap in assembled relation on the patient.

2. The protective case of claim 1 wherein said belt clip has a generally U-shaped configuration defining a pair of legs for snap-fit mounting respectively over said closed end of said housing and said seal cap at said open end of said housing.

3. The protective case of claim 2 wherein said closed end of said housing and said seal cap include shallow channels formed therein for seated reception of said belt clip legs.

4. The protective case of claim 2 wherein said closed end of said housing and at least one of said belt clip legs include interlocking key and keyway means for securely interconnecting said at least one belt clip leg with said closed end of said housing.

5. The protective case of claim 1 wherein said shock absorber means comprises at least one resilient bumper mounted within said housing at least one resilient bumper mounted within said housing at the closed end thereof.

6. A protective case for a medication infusion pump having a catheter tube extending therefrom for delivery of a selected medication from he pump to a patient, said protective case comprising:
   a housing formed from an impact resistant material, said housing having one closed end and an opposite open end;
   shock absorber means for resiliently supporting the pump within said housing; and
   a seal cap removably mounted on said housing over said open end thereof, said seal cap having a catheter port formed therein for sealed passage of the catheter tube from the pump to the exterior of said housing;
   said shock absorber means comprising a generally cup-shaped resilient boot mounted within said housing at the closed end thereof and defining a cavity for seated reception of one end of the pump.

7. The protective case of claim 6 wherein said shock absorber means further comprises a generally cup-shaped cavity defined by a portion of said seal cap for seated reception of an opposite end of the pump.

8. A protective case for a medication infusion pump having a catheter tube extending therefrom for delivery of a selected medication from the pump to a patient, said protective case comprising:
   a housing formed from an impact resistant material, said housing having one closed end and an opposite open end;
   shock absorber means for resiliently supporting the pump within said housing; and
   a seal cap removably mounted on said housing over said open end thereof, said seal cap having a catheter port formed therein for sealed passage of the catheter tube from the pump to the exterior of said housing;
   said seal cap being formed from a resilient elastomer, said seal cap defining a side slit opening into said catheter port to permit the catheter tube to be drawn into said catheter port, said seal cap sealingly engaging the catheter tube and sealingly closing the side slit when said seal cap is mounted on the housing.

9. A protective case for a medication infusion pump having a catheter tube extending from a first end thereof for delivery of a selected medication from the pump to a patient, said protective case comprising:
   an impact resistant housing defining a closed end wall at one end thereof, and an opposite open end;
   shock absorber means disposed within said housing generally at said closed end wall, said shock absorber means defining a generally cup-shaped cavity for seated reception of a second end of the pump upon slide-fit reception of the pump into said housing, said shock absorber means maintaining said pump second end in spaced relation with said housing; and
   a resilient seal cap removably mounted on said housing at the open end thereof, said seal cap cooperating with said housing to define a substantially watertight enclosure, said seal cap including means defining a generally cup-shaped cavity for seated reception of said first end of the pump to maintain the pump first end in spaced relation with said housing;
   said seal cap having a catheter port formed therein for seated and sealed passage of the catheter tube from the pump to the exterior of said housing.

10. The protective case of claim 9 further including means for retaining said seal cap on said housing.

11. The protective case of claim 10 wherein said retaining means comprises a belt clip, and further including a belt for removable connection to said belt clip, said belt being adapted to support said belt clip together with said housing and said seal cap in assembled relation on the patient.

12. The protective case of claim 11 wherein said belt clip has a generally U-shaped configuration defining a pair of legs for snap-fit mounting respectively over said closed end wall of said housing and said seal cap at said open end of said housing.

13. The protective case of claim 12 wherein said closed end wall of said housing and said seal cap include shallow channels formed therein for seated reception of said belt clip legs.

14. The protective case of claim 12 wherein said closed end wall of said housing and at least one of said belt clip legs include interlocking key and keyway means for securely interconnecting said at least one belt clip leg with said closed end wall of said housing.

15. The protective case of claim 9 wherein said shock absorber means further includes at least one resilient bumper mounted within said housing on said closed end wall for resiliently contacting said second end of the pump.

16. The protective case of claim 9 wherein said seal cap has a side slit formed therein and opening into said catheter port, said seal cap sealingly engaging the catheter tube and sealingly closing the side slit when said seal cap is mounted on the housing.

17. The protective case of claim 9 wherein the pump has a luer fitting at said first end for connection to the catheter tube, said cavity defined by said seal cap including a first portion of larger cross sectional size for seated reception of said pump first end, and a second portion of smaller cross sectional size within which the luer fitting is disposed when said seal cap is mounted onto said housing with the pump disposed within said housing.

* * * * *